(12) United States Patent
Kiel et al.

(10) Patent No.: US 7,786,168 B2
(45) Date of Patent: *Aug. 31, 2010

(54) PHENOLIC ACID SALTS OF GABAPENTIN IN SOLID DOSAGE FORMS AND METHODS OF USE

(75) Inventors: Jeffrey S. Kiel, Gainesville, GA (US); H. Greg Thomas, Villa Rica, GA (US); Narasimhan Mani, Port Jefferson, NY (US)

(73) Assignee: Kiel Laboratories, Inc., Gainesville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/138,945

(22) Filed: Jun. 13, 2008

(65) Prior Publication Data

US 2008/0242728 A1 Oct. 2, 2008

Related U.S. Application Data

(63) Continuation of application No. 10/805,806, filed on Mar. 22, 2004, now Pat. No. 7,456,312.

(60) Provisional application No. 60/457,399, filed on Mar. 25, 2003.

(51) Int. Cl.
A61K 31/196 (2006.01)
C07C 61/08 (2006.01)

(52) U.S. Cl. .................. 514/561; 562/507
(58) Field of Classification Search ........... 562/507; 514/561
See application file for complete search history.

(56) References Cited

U.S. PATENT DOCUMENTS

| | | | |
|---|---|---|---|
| 2,397,799 A | 4/1946 | Martin et al. | |
| 2,421,714 A | 6/1947 | Rieveschl | |
| 2,950,309 A | 8/1960 | Cavallito | |
| 3,282,789 A | 11/1966 | Marty et al. | |
| 4,024,175 A | 5/1977 | Satzinger et al. | |
| 4,309,989 A | 1/1982 | Fahim | |
| 4,552,899 A | 11/1985 | Sunshine et al. | |
| 4,619,934 A | 10/1986 | Sunshine et al. | |
| 4,749,697 A | 6/1988 | Sunshine et al. | |
| 4,749,711 A | 6/1988 | Sunshine et al. | |
| 4,749,721 A | 6/1988 | Sunshine et al. | |
| 4,749,722 A | 6/1988 | Sunshine et al. | |
| 4,749,723 A | 6/1988 | Sunshine et al. | |
| 4,767,402 A | 8/1988 | Kost et al. | |
| 4,839,354 A | 6/1989 | Sunshine et al. | |
| 5,025,019 A | 6/1991 | Sunshine et al. | |
| 5,068,413 A | 11/1991 | Steiner et al. | |
| 5,095,148 A | 3/1992 | Mettler et al. | |
| 5,132,451 A | 7/1992 | Jennings et al. | |
| 5,164,398 A | 11/1992 | Sims et al. | |
| 5,560,933 A | 10/1996 | Soon-Shiong et al. | |
| 5,599,846 A | 2/1997 | Chopdekar et al. | |
| 5,614,178 A | 3/1997 | Bloom et al. | |
| 5,663,415 A | 9/1997 | Chopdekar et al. | |
| 5,759,579 A | 6/1998 | Singh et al. | |
| 5,948,414 A | 9/1999 | Wiersma | |
| 6,037,358 A | 3/2000 | Gordziel | |
| 6,063,770 A | 5/2000 | Falcon | |
| 6,083,490 A | 7/2000 | Ellis et al. | |
| 6,117,452 A | 9/2000 | Ahlgren et al. | |
| 6,187,315 B1 | 2/2001 | Falcon | |
| 6,248,363 B1 | 6/2001 | Patel et al. | |
| 6,287,597 B1 | 9/2001 | Gordziel | |
| 6,306,904 B1 | 10/2001 | Gordziel | |
| 6,383,471 B1 | 5/2002 | Chen et al. | |
| 6,403,119 B2 | 6/2002 | Oppenheim et al. | |
| 6,417,206 B1 | 7/2002 | Leflein et al. | |
| 6,462,094 B1 | 10/2002 | Dang et al. | |
| 6,509,492 B1 | 1/2003 | Venkataraman | |
| 6,703,044 B1 | 3/2004 | Pinhasi et al. | |
| 6,740,312 B2 | 5/2004 | Chopin et al. | |
| 7,141,606 B2 * | 11/2006 | Bryans et al. | 514/511 |
| 7,390,922 B2 * | 6/2008 | Kiel et al. | 562/507 |
| 7,456,312 B2 * | 11/2008 | Kiel et al. | 562/507 |
| 2003/0050252 A1 | 3/2003 | Kiel et al. | |
| 2003/0077321 A1 | 4/2003 | Kiel et al. | |
| 2004/0192617 A1 | 9/2004 | Kiel et al. | |
| 2004/0192618 A1 | 9/2004 | Kiel et al. | |

FOREIGN PATENT DOCUMENTS

WO  WO 01/13894 A1  3/2001
WO  WO 2004/032826 A2  4/2004

OTHER PUBLICATIONS

Berge et al , Journal of Pharmaceutical Sciences, 66, No. 1, Jan. 1977., p. 1-18.*
Cypress Pharmaceutical, Inc., "R-Tannic-S A/D," RX Only, Cypress Pharmaceutical, Inc., (Madison, MS), p. 1, 2 (Mar. 1, 2001).
DSC Laboratories, "Phenylephrine Tannate/Pyrilamine Tannate Suspension," RX Only, DSC Laboratories (Muskegon, MI), p. 1, 2 (Aug. 1, 2001).
Goldberg, Ronald M.D. and Shuman, Franklin M.D., "Evaluation of a Prolonged Action Oral Antihistaminic Preparation as Treatment for Allergic Disorders," Clinical Report, Clinical Medicine (Washington), vol. 72 (No. 9), pp. 1475-1479 (Sep. 1, 1965).
Weiler, John M.D., et al., "Randomized, double-blind, parallel groups, placebo-controlled study of efficacy adn safety of Rynatan in the treatment of allergic rhinitis using an acute model," Annals of Allergy, ACAI (Iowa City, IA), vol. 64 (No. 1), p. 63-67 (Jan. 1, 1990).

* cited by examiner

Primary Examiner—Taylor Victor Oh
(74) Attorney, Agent, or Firm—King & Schickli, PLLC

(57) ABSTRACT

The present invention relates to pharmaceutical compositions of gabapentin tannate in solid dosage form, processes for production of those compositions and methods of use of those compositions. Tannate salts of active pharmaceutical ingredients are used in sustained release applications and to improve certain organoleptic properties such as taste. The process may utilize either natural or synthetic tannic acid.

9 Claims, No Drawings

PHENOLIC ACID SALTS OF GABAPENTIN IN SOLID DOSAGE FORMS AND METHODS OF USE

This application is a continuation of U.S. patent application Ser. No. 10/805,806 filed Mar. 22, 2004 now U.S. Pat. No. 7,456,312 which claims the benefit of U.S. Provisional Patent Application Ser. No. 60/457,399 filed on Mar. 25, 2003.

TECHNICAL FIELD AND INDUSTRIAL APPLICABILITY OF THE INVENTION

The present invention relates generally to the field of tannate chemistry and more specifically to solid dosage forms of gabapentin tannate and related methods of use.

BACKGROUND OF THE INVENTION

The literature describes many ways of preparing gabapentin from a variety of starting materials, as the hydrochloride hydrate, the monohydrate and the sodium salt forms. However, the prior art neither discloses nor suggests the preparation of gabapentin tannate. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt. Further, none of these references mention the preparation and incorporation of gabapentin tannate into suitable dosage forms for pharmaceutical use.

SUMMARY OF THE INVENTION

In accordance with the object of the present invention a process is provided for preparing a pharmaceutical composition for treating a condition of the central nervous system in a mammalian subject. That process comprises reacting gabapentin with tannic acid to produce a pharmaceutically effective amount of gabapentin tannate in solid dosage form.

Naturally occurring tannic acid comprises a mixture of compounds. They are considered to be secondary metabolites, with a molecular weight of 500-5000 Da, that have no specific metabolic function. As with many natural polymers, a rigorous chemical definition of tannins is difficult.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

The process may be further described as including one or more pharmaceutically acceptable excipients. The excipients may be selected from a group consisting of an anti-clumping agent, a filler, a diluent, a colorant, a sweetening agent, a lubricant, a binding agent, a disintegrating agent, a flavoring agent and mixtures thereof. Further, the process includes the steps of providing the pharmaceutically effective amount of gabapentin tannate in solid dosage form. Further, the process may be completed by means of in-situ conversion of gabapentin to gabapentin tannate.

In accordance with another object of the present invention, a method is provided for treating a condition of the central nervous system in a mammalian subject. The method comprises administering a pharmaceutically effective amount of gabapentin tannate in solid dosage form. The administration may be done orally. The method may be further described as administering between about 0.1 to about 3600 mg of gabapentin in gabapentin tannate salt form per day.

DETAILED DESCRIPTION OF THE PREFERRED EMBODIMENTS OF THE INVENTION

The present invention provides a method of preparation and use of gabapentin tannate in solid dosage form.

Gabapentin is a neuroleptic agent indicated as adjunctive therapy in the treatment of central nervous system conditions in mammalian subjects such as partial seizures, with and without secondary generalization, epilepsy, faintness attacks, hypokinesis, pain associated with shingles and cranial traumas. Gabapentin is a white to off-white crystalline solid and is a polymorphic substance. It is freely soluble in water and across a wide range of pH and is characterized by a marked bitter taste. Chemically, gabapentin is 1-(amino methyl) cyclohexaneacetic acid with the empirical formula $C_9H_{17}NO_2$ and a MW of 171.24. Typically, gabapentin is administered in multiple doses for optimal pharmacological action.

The literature describes many ways of preparing gabapentin from a variety of starting materials. U.S. Pat. No. 4,024,175 describes at least three methods of preparing gabapentin from cyclohexyl-1,1-diacetic acid. Each of these methods results in the formation of gabapentin hydrochloride salt, which may be converted to 1-(aminomethyl)-1-cyclohexaneacetic acid by treatment with a basic ion exchanger and then crystallized from a solvent such as ethanol/ether.

Alternative methods for preparing gabapentin have been described that do not proceed via the hydrochloride or any other mineral acid salt. Such methods include those described in U.S. Pat. Nos. 5,132,451, 5,095,148, and 5,068,413. Each of these methods involves a cyanic intermediate, which is hydrogenated under severe conditions to produce the free amino acid.

However, the prior art neither discloses nor suggests the preparation of gabapentin tannate. The formation of a tannate salt of gabapentin is unexpected because of the close proximity of a carboxylic acid group to the amine group. The negative charge on the carboxylic acid group was expected to shield and possibly neutralize the positive charge on the proximal nitrogen. Since tannate salts are thought to normally form through an ionic interaction with a positively charged amine functional group, the close proximity of the carboxylic acid group was expected to prevent the formation of the tannate salt.

Gabapentin is structurally related to the neurotransmitter γ-aminobutyric acid (GABA) but unlike GABA, is able to cross the blood-brain barrier. Although its exact mechanism of action remains unclear gabapentin was recently shown to be a selective agonist at the gb1a-gb$^2$ heterodimer and post-synaptic GABA$_B$ receptor, a newly identified receptor subtype. The pharmacokinetics of gabapentin have been well characterized in adults. Peak plasma gabapentin concentrations occur 2-3 hours post-dose. The absolute bioavailability of gabapentin is approximately 60% after administration of 300 mg and is dose-dependent. While steady-state plasma gabapentin concentrations increased with increasing doses, the increase is not proportional to dose possibly due to saturation of the active transport across the gut via the L-amino acid transporter. Gabapentin does not bind to plasma proteins and is not metabolized. Gabapentin is eliminated via glomerular filtration, and dosage adjustment is necessary in patients with renal impairment. In subjects with normal renal function, gabapentin elimination half-life averages between 5 and 7 h. Dosing recommendations are 900-1800 mg/day for anticonvulsant activity and panic disorders may require dosages in the range of between about 3000 to 3600 mg/day of gabapentin. The bioavailability and high dosage requirements for pharmacological action stipulate multiple dosings of gabapentin.

Naturally occurring tannic acid comprises a mixture of compounds. They are considered to be secondary metabolites, with a molecular weight of 500-5000 Da, that have no specific metabolic function. They are complex phenol-rich polymers found in many foods. As with many natural polymers, a rigorous chemical definition of tannins is difficult. In general two classes are distinguished—the hydrolyzable and the condensed tannins. Hydrolyzable tannins or tannic acids are referenced in the various pharmacopeias and are composed of gallic acid or its condensation product ellagic acid esterified to the hydroxyl groups of glucose.

Hydrolyzable tannins are molecules with a polyol (generally D-glucose) as a central core, with the hydroxyl groups of the carbohydrate partially or totally esterified with phenolic groups. They derive their name from their propensity to be hydrolyzed by mild acids or mild bases to yield carbohydrates and phenolic acids. Synthetic tannic acid may comprise a purified form of any of the components of naturally occurring tannic acid.

The present invention may utilize tannic acid of either a natural or synthetic source. The term "tannic acid" herein refers to either natural or synthetic tannic acid as described above.

Tannic acid elicits a characteristic astringent taste. A pH independent decrease in measures of amiloride-sensitive sodium channels in the tongue, which are regarded as conveying salty taste, has been observed when tannic acid was applied to the lingual surface. Physiologically, it has been demonstrated that there is a pH independent inhibition of chorda tympani responses to bitter and salty stimuli in the presence of tannic acid. The above mechanism of action has been used to explain experimental results which showed a taste suppression of 100% by tannic acid, of compounds like quinine HCl, papaverine HCl (bitter tasting compounds), NaCl (salty) and tartaric acid (sour).

The formation of the tannate salt is by the reaction of the amine groups (in the 1°, 2°, 3°, 4° or amphoteric functional states) or of other basic functional groups with the carboxylic and hydroxyl groups present in tannic acid. For example, the amine groups of the API could react covalently with the hydroxyl groups of tannic acid by an oxime formation or by the ionization of the tannic acid and the protonation of the nitrogen atom in the amine group to form an ionic bond, generating the tannate salt. In the present invention the active ingredient gabapentin is present in zwitter-ionic form. The protonated nitrogen reacts with tannic acid to form the tannate salt.

The ratio of the gabapentin to tannic acid is important for optimizing the efficiency of the reaction to form the tannate salt. Typically, tannic acid needs to be present in a concentration of at least one half to five-fold that of the tannic acid by weight. The dispersing or anti-clumping agents used are naturally occurring gums or other polymers used as thickening agents. The dispersing or anti-clumping agent serves as an adherent or a solid support for the tannic acid molecules to facilitate the reaction between the gabapentin and tannic acid. In addition it also prevents the clumping and aggregation of the tannate salt formed, which aids in the uniform distribution of the precipitate in the mixture. The synthetic process can be used as a conversion method for generating tannate salts of gabapentin and is a novel way of directly incorporating them into suitable solid dosage forms.

By starting with a commonly available form of gabapentin, which is converted to a tannate salt, the invention provides an efficient and reproducible method to manufacture products containing gabapentin tannate as an active ingredient. The tannate salt of the gabapentin also possesses better organoleptic properties, such as taste.

Using the present invention, gabapentin tannate may be prepared in the form of powders, capsules, and the preferred form of tablets formulated so that ideally each tablet contains about 0.1 mg to about 3600 mg, of gabapentin in the tannate salt. A preferred way of preparing the tannate salt of gabapentin is by reacting the aqueous solution or the powder form of the drug with a tannic acid mixture in liquid or powder form, without the use of volatile solvents. Typically, the tannic acid is provided at a weight $W_1$ and the gabapentin at a weight $W_2$ wherein $W_1$ is from about 0.05 to about 20 times $W_2$. Any anti-clumping agent is provided at a concentration of about 0.01 to about 95% by weight of the final composition. The pH is typically maintained in a range of about 2.0 to about 11.0. The tannate salt prepared can then be directly incorporated into suitable pharmaceutically effective dosage forms without further purification and isolation.

Tablets containing gabapentin tannate are prepared by the addition of one or more suitable pharmaceutical carriers or excipients including fillers, diluents, colorants, lubricants, flavoring agents, sweetening agents and the like as well as conventional and well known binding and disintegrating agents. A typical tablet composition of the present invention containing starch, dibasic calcium phosphate, coloring agent, microcrystalline cellulose, magnesium aluminum silicate, magnesium stearate, methylcellulose, sucrose, HPMC and talc as described in Example 1 is prepared as follows:

EXAMPLE 1

| Gabapentin Tannate Tablets | |
|---|---|
| Ingredient | Milligrams per tablet |
| Gabapentin Tannate | 900.0 |
| Starch, NF | 4.5 |
| HPMC | 6.7 |
| Magnesium Aluminum Silicate | 6.7 |
| Dibasic Calcium Phosphate | 13.7 |
| Compressible sugar (DIPAC) | 244.2 |
| Microcrystalline cellulose (Avicel PH 102) | 157.0 |
| Talc | 13.5 |
| FD&C Blue #2 Aluminum Lake | 2.7 |
| Magnesium Stearate | 13.5 |

The conversion process used to synthesize the tannate salt of the active is performed at room temperature using the following procedure. About 50 ml of purified water is placed in a suitable vessel and the active is added to the water and stirred to dissolve. Microcrystalline cellulose, tannic acid and magnesium aluminum silicate are placed in a suitable container and mixed. The solution of gabapentin is added onto the powders while mixing and mixing is continued for 10-15 minutes, to obtain the gabapentin tannate salt.

The powder mass of the gabapentin tannate salt can be directly wet granulated by the addition of one or more suitable excipients. The granulation is subsequently dried and dry blended with more diluent, sweetening, hardness increasing, and coloring agents as necessary.

Capsules containing the unique tannate compound of the present invention are prepared by the addition of suitable pharmaceutical carriers including glidants, lubricants and the like. A typical capsule composition of the present invention containing talc and, magnesium stearate as described in Example 2 is prepared as follows:

EXAMPLE 2

Gabapentin Tannate Capsules

| Ingredient | Milligrams per capsule |
|---|---|
| Gabapentin Tannate | 2500.0 |
| Talc | 13.5 |
| Magnesium Stearate | 13.5 |

The conversion process used to synthesize the tannate salt of the active is performed at room temperature using the following procedure. Gabapentin and tannic acid are placed in a suitable mixer or blender and mixed for a period of 10 minutes to obtain a powder blend. 100 ml of purified water is added onto the powders while and mixing is continued for 10-15 minutes, to obtain the gabapentin tannate salt.

The powder mass of the gabapentin tannate salt can be directly mixed with more diluent, and flow agents as necessary. A typical capsule composition prepared is shown above.

The dosage administered will be dependent on the age, health and weight of the recipient, kinds of concurrent treatment, if any, frequency of treatment and desired effect.

What is claimed:

1. A gabapentin tannate pharmaceutical composition comprising as an active ingredient a pharmaceutically effective amount of gabapentin tannate in solid dosage form wherein the tannic acid component is of either natural or synthetic origin.

2. The composition of claim 1 further including one or more pharmaceutical excipients.

3. The composition of claim 2, wherein said excipients are selected from a group consisting of an anti-clumping agent, a filler, a diluent, a colorant, a sweetening agent, a lubricant, a binding agent, a disintegrating agent, a flavoring agent and mixtures thereof.

4. The composition of claim 2, wherein said composition further includes one or more solvents selected from a group consisting of water, purified water, ethanol, isopropyl alcohol, glycerin, propylene glycol, mineral oil and mixtures thereof.

5. The composition of claim 2, wherein said one or more excipients are sweetening agents selected from a group consisting of sucrose, saccharin sodium, aspartame, sucralose and mixtures thereof.

6. The composition of claim 2, wherein said one or more excipients are anti-clumping agents selected from a group consisting of magnesium aluminum silicate, xanthan gum, polyvinylpyrrolidone, cellulose compounds, magnesium stearate, colloidal silica, talc, stearic acid, calcium stearate, lactose, mannitol, sucrose and mixtures thereof.

7. A method of treating a condition of the central nervous system in a mammalian subject wherein said condition of the central nervous system is selected from a group consisting of partial seizures, epilepsy, faintness attacks, hypokinesis, pain associated with shingles and cranial trauma, comprising administering a pharmaceutically effective amount of gabapentin tannate in solid dosage form.

8. The method of claim 7 wherein said administering step is performed orally.

9. The method of claim 7, including providing between about 0.1 to about 3600 mg of gabapentin in gabapentin tannate salt form.

* * * * *